United States Patent [19]

Matory

[11] Patent Number: 5,429,593

[45] Date of Patent: Jul. 4, 1995

[54] POST-SURGICAL, DRAINAGE ACCOMMODATING, COMPRESSION DRESSING

[76] Inventor: Yvedt L. Matory, 22 May St., Boston, Mass. 02130

[21] Appl. No.: 173,206

[22] Filed: Dec. 23, 1993

[51] Int. Cl.⁶ .................... A61F 13/00; A61F 15/00
[52] U.S. Cl. ........................... 602/79; 2/114;
    2/73; 450/58; 450/1; 602/53; 602/61
[58] Field of Search .............. 604/345; 602/79, 53,
    602/61; 128/874, 846, 845; 450/1, 30–32, 58,
    79, 80, 91, 85; 2/114, 73; 606/201

[56] References Cited

U.S. PATENT DOCUMENTS

| | | | |
|---|---|---|---|
| 3,075,531 | 1/1963 | Clover | 450/67 |
| 3,173,420 | 3/1965 | Mazzoni et al. | 450/58 |
| 3,561,442 | 2/1971 | Goswitz | 450/1 |
| 3,628,539 | 12/1971 | Fredricks | 450/80 |
| 3,895,629 | 7/1975 | Snyder | 602/79 |
| 3,968,803 | 7/1976 | Hyman | 602/79 |
| 4,698,848 | 10/1987 | Buckley | 2/114 |
| 4,718,124 | 1/1988 | Sawicki et al. | 2/114 |
| 5,048,122 | 9/1991 | Prieur | 2/114 |
| 5,142,702 | 9/1992 | Piloian | 604/345 |
| 5,152,741 | 10/1992 | Farnio | 602/79 |
| 5,180,376 | 1/1993 | Williams | 450/31 |
| 5,257,956 | 11/1993 | Ewen | 450/1 |

Primary Examiner—Robert A. Hafer
Assistant Examiner—Michael O'Neill
Attorney, Agent, or Firm—David Prashker

[57] ABSTRACT

The present invention provides a post-surgical, drainage accomodating, compression dressing and garment intended to be worn by a man or woman after chest wall surgery to cover and compress at least one surgical incision site on the upper torso. The dressing is formed at least in part by deformable elastomeric material for the generation of compression forces over the surgical incision and over the surrounding upper torso areas. This improved garment provides for the presence of a surgical drain for the collection of fluids, the drain extending from the surgical incision site into the external ambient environment; and can also provide a support for a drainage collection bulb which is often present as part of the surgical drainage system.

11 Claims, 8 Drawing Sheets

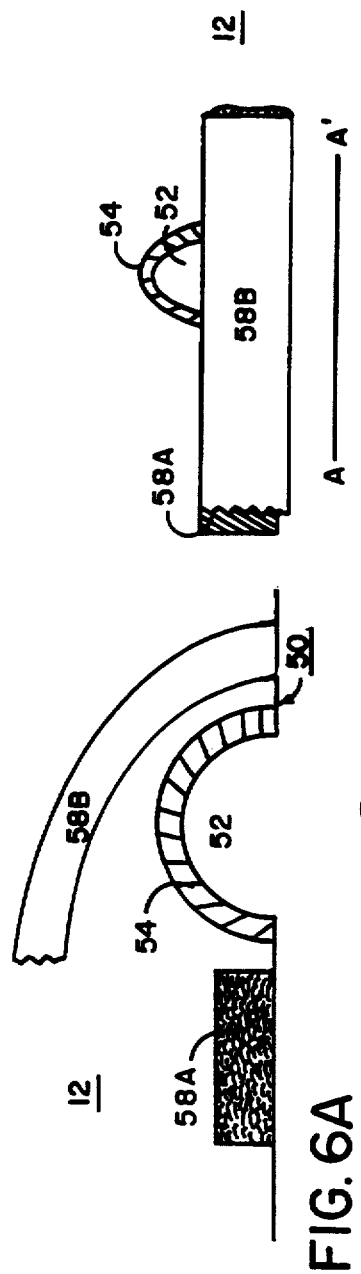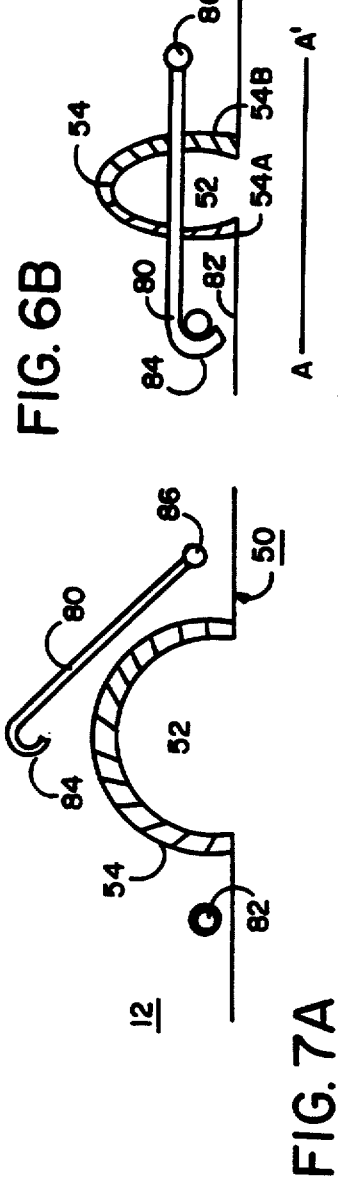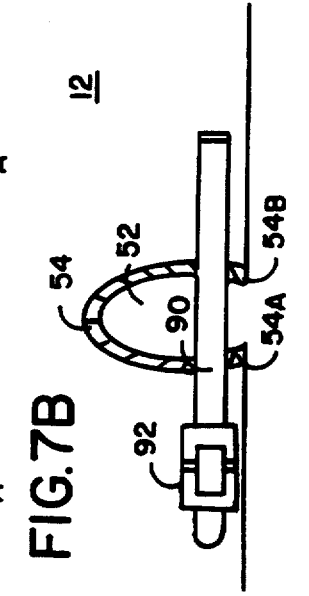

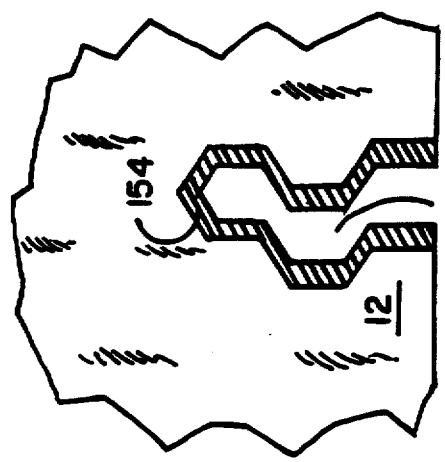
FIG. 9E
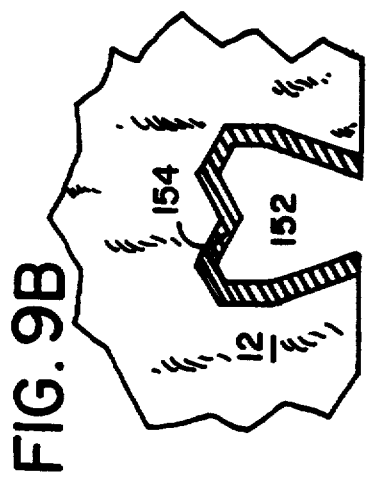
FIG. 9B
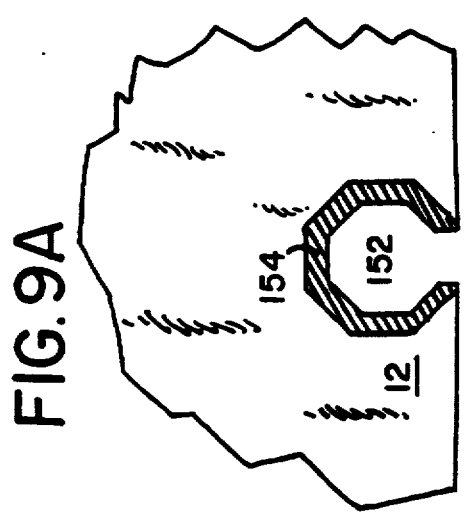
FIG. 9A
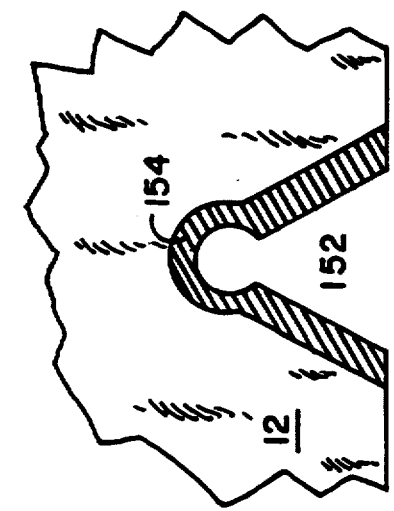
FIG. 9C
FIG. 9D

POST-SURGICAL, DRAINAGE ACCOMMODATING, COMPRESSION DRESSING

FIELD OF THE INVENTION

The present invention is concerned generally with compression generating garments to be worn by men and women after chest wall, breast or underarm surgery during the recovery and convalescent stages.

BACKGROUND OF THE INVENTION

Two significant problems occur immediately following surgery on the chest, breast or underarm. The first is bleeding which is most common during the first 24 hours. The second is accumulation of lymphatic fluid (a clear yellow protein containing fluid) most common during the first two weeks after surgery.

Bleeding is prevented by careful surgical technique during the operation and by chest wall compression post-operatively. Direct compression force against the incision markedly reduces bleeding and promotes healing. For these reasons, surgeons routinely place surgical padding and tape against the incision to generate compression force over an indefinite period of time. The most frequently used dressing after breast surgery is gauze and tape. Unfortunately, the use of tape can be painful for patients during recovery and convalescence; and when the tape is removed, typically a layer of skin is also removed along with the tape. As a result, the use of tape frequently leaves small bruises or blisters on the skin. As an alternative, elastic bandages have also been employed for use as wrappings across the chest following chest wall or breast surgery. The use of such elastic bandages also is usually uncomfortable for the patient; and can restrict the patient's breathing if the wrapping is applied too tightly.

Lymphatic fluid production cannot be prevented and causes delayed healing if not drained. Typically, after mastectomy, lumpectomy, or after surgery on the chest wall or underarm, one or more surgical drains are placed near the surgical incision to collect these fluids and other matter that accumulate. Such drains and drainage systems of varying kinds conventionally are formed of soft tubing which exits the chest wall and drain individually or collectively into a collection bulb similar to that found on a meat basting syringe. The liquids and small solid matter particles collect in this bulb. The collection bulb, growing heavier with the accumulating fluid, typically must be supported or it will pull away from the body and disturb or completely rupture the drains resting within the surgical wound. Moreover, even in those instances where a collection bulb is not present within the drainage apparatus or system, the entirety of the drainage assembly exiting the surgical incision site must be accommodated, protected and supported throughout the recovery and convalescence of the patient.

It will be recognized and appreciated that although there are several garments and support articles conventionally known and medically employed after surgery for patients undergoing chest wall surgery, none of these, insofar as is presently known, offer solutions for accommodating the fluid drains and drainage systems used routinely in surgical practice for the removal of fluids after surgery. To the contrary, the conventionally known dressings, supports, bandages, and brassieres are directed primarily toward prosthetic applications and uses. Merely representative of these conventionally known articles and devices are the following: a breast support for post-surgical used for open heart surgery patient as described by U.S. Pat. No. 4,391,277; a therapeutic chest dressing for breasts having implants as disclosed by U.S. Pat. No. 5,098,331; a surgical brassiere for reducing stress along a midsternal incisional line of a female patient following cardiothoracic surgery as described by U.S. Pat. No. 4,804,351; a reversible mastectomy brassiere which provides a prosthesis on the left or right breast as shown by U.S. Pat. No. 5,180,326; and a mastectomy surgical brassiere for retaining surgical dressings over the incision lines of a single or double mastectomy as disclosed by U.S. Pat. No. 5,158,541. These representative examples illustrate the range and variety of garments and devices that do not recognize the recurring problems of accommodating drainage fluid removing systems after surgery. In addition, the above items do not include a comfortable, safe, and painless means of providing compression on the chest wall.

Accordingly, it will be recognized and appreciated that there has been a longstanding need for a garment which may be worn by a male or female patient immediately after chest wall surgery generally or after surgery on the underarm or breast specifically, which will accommodate surgical drains exiting from the incision site in a manner which will avoid chest wall binding, disruption or separation of the drain from the chest wall. In addition, if such a garment were also able to provide compression force over the torso generally and over the surgical incision site in particular to prevent bleeding, such a construction and article would be recognized by physicians as a major advance and unexpected improvement in this art.

BRIEF DESCRIPTION OF THE FIGURES

The present invention may be more easily and completely understood when taken in conjunction with the accompanying drawing, in which:

FIGS. 6A and 6B are detailed views of the on-demand juncture means comprising the cutout zone of the embodiment of FIG. 1;

FIGS. 7A and 7B are detailed views of one alternative on-demand juncture means for the cutout zone;

FIGS. 8A and 8B are detailed views of another alternative on-demand juncture means for the cutout zone;

FIGS. 9A-9E are detailed views of alternative apertures and marginal edgings for the cutout zone;

DETAILED DESCRIPTION OF THE PRESENT INVENTION

Figure 1:
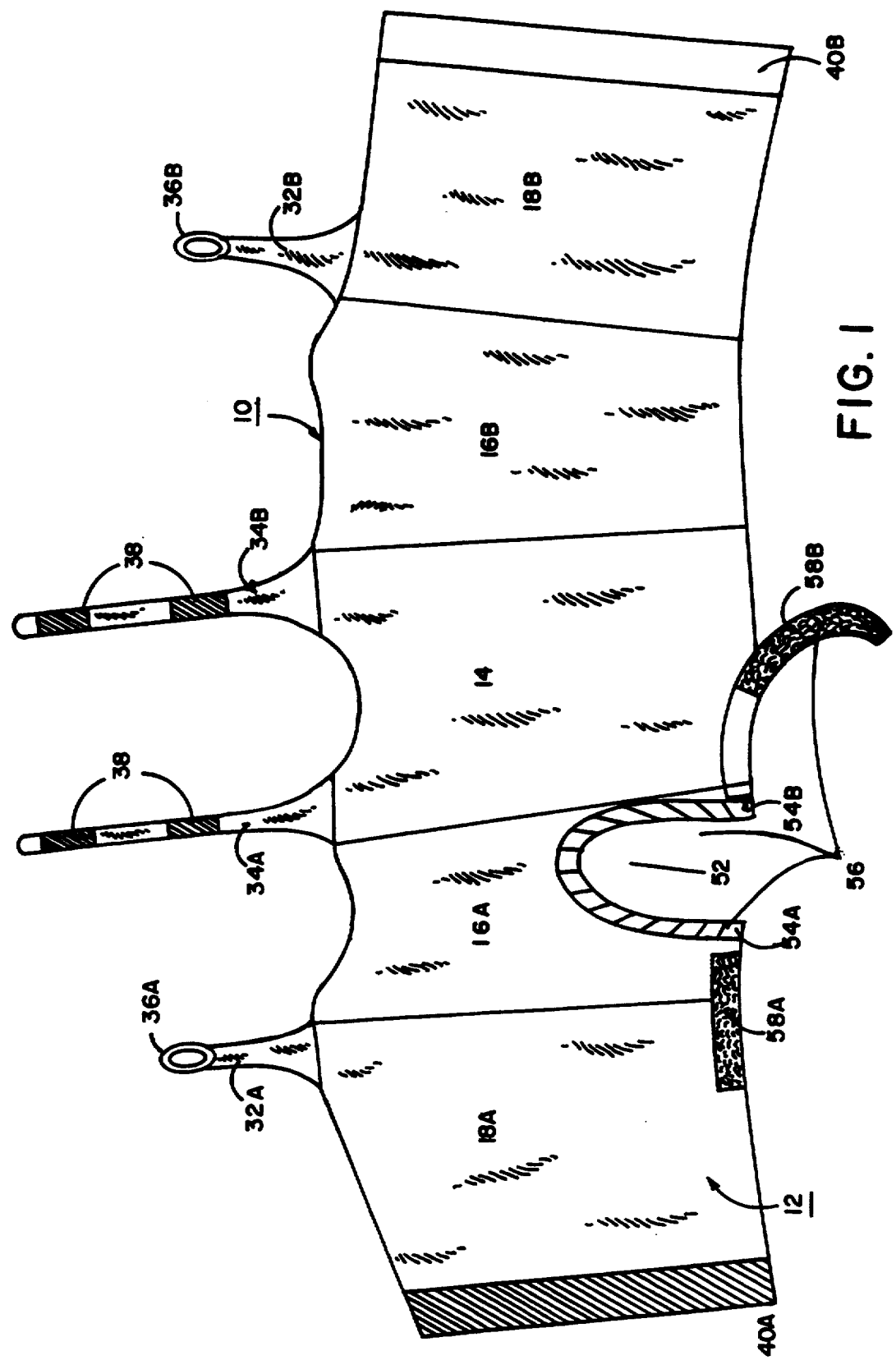
FIG. 1 is an overhead view of a first preferred embodiment of the present invention as a flat, unworn, garment.

The present invention is a drain accommodating, compression force generating, dressing intended to be worn by a male or female patient immediately after chest wall or breast surgery; and which will continue to be worn during the recovery and convalescence of the patient over the weeks and months following the surgery. When constructed in the manner described hereinafter, this invention has unique structural features, unexpected capabilities, and desirable advantages. These include the following:

1. The improved dressing which is the present invention may be effectively and advantageously used by both male and female patients after undergoing any kind of degree of chest wall, breast, or underarm surgery. The instances of usage thus include but are not limited to chest wall reconstructive surgery such as trans-abdominal muscle flaps and latissimus dorsal flaps (plastic surgery); axillary node dissection; mastectomy; partial mastectomy; and lumpectomy.

2. This improved dressing is constructed of deformable elastomeric materials and will provide compression forces over the entire torso area upon which it is positioned and worn. The invention thus comprises a torso compression bandage which is positioned over the surgical incision site as well as the immediately adjacent or surrounding areas of the body. The compression force generating capability of this improved dressing eliminates the need for using tape and the tape burns, bruises and blisters on the skin associated with tape removal; and also eliminates the need for elastic wrappings and compression bandages which are often uncomfortable for the patient and frequently restrict breathing for the patient when wrongly applied. The compression forces generated by the present invention will provide adequate force on the incision to promote healing and prevent bleeding and also provides ease and comfort for the patient.

3. Each embodiment of the present invention comprises a deformable cutout zone which functions as an exit for the surgical drains and drainage assembly positioned within the incision site and passing through the gauze bandage immediately covering the incision and the surrounding skin area. The presence and use of the cutout zone avoids the drain and drainage assembly from being pushed up against the chest wall, an event which is both irritating and uncomfortable; and this cutout zone prevents the drains and drainage assembly from being dislocated or ruptured accidentally as a consequence of the patient wearing conventionally known garments. As is described in detail hereinafter, each cutout zone comprises an expandable and contractible aperture, at least one elastic and compression generating marginal edging which delineates the perimeter and size of the aperture, and provides on-demand juncture means for on-demand joining of a part of the marginal edging to the remainder of the dressing.

4. The improved dressing and the requisite cutout zone appearing in each embodiment is not only able to provide passage for at least one surgical drain or drainage assembly from within the surgical incision site through the fabric of the dressing itself out into the external ambient environment, but also provides the structural means for generating an additional compression force around the perimeter of the aperture through which the drains and drainage assembly exits. By this construction and design, the existence of an expandable and contractible exit through which a surgical drain or drainage assembly may pass from the interior of the surgical incision site into the external ambient environment does not meaningfully detract from or reduce the capability of the improved dressing to generate compression force on the torso even at the exit site itself.

5. The present invention may be manufactured as a single, one piece article or formed from multiple parts as an integrated one piece assembly. The dimensions, configuration, and overall surface area presented by this improved dressing may be varied to suit the needs and requirements of the surgical procedure and/or to suit the individual needs or desires of the male or female patient. Thus, the surface area of the torso and concomitantly the total surface over which compression force will be generated and applied, may vary from a relatively narrow coverage across the mid-chest area, the breasts, and back; or constitute a complete coverage of chest, shoulders, body sides and back of the patient from the neck to the pelvis.

6. The present invention is a dressing, a therapeutic covering, designed to provide both elasticity and compression force. As a result, in most embodiments, the dressing will not have clearly defined sections or constructions over the breasts and chest. Instead, the improved dressing will typically take form as one flat transverse band of elastic fabric which is positioned around the chest and back to cover the breasts of the patient and provide compression force over the torso via the deformation of the elastomeric materials forming the fabric itself. In other specific instances, a clearly defined cup of multiple sections may be found desirable, especially for female patients after surgical procedures which do not directly involve the breasts; and several embodiments are envisioned and intended which permit the user to provide defined breast cups of various volumes to accommodate the comfort and needs of the female patient. These alternative embodiments provide support for the non-operated breast and relieve incisional pain brought on by the weight of the operated breast.

7. One preferred embodiment of the present invention employs the use of compression-generating shoulder harnesses comprising a plurality of flap members which are attached and detached from one another on-demand. The presence of such shoulder harness constructions is a desirable alternative to the use of the narrow shoulder straps conventionally used with brassieres. Embodiments of the shoulder harnesses are broad in size and typically extend in width from the neck to the shoulder line; and individually will cover each shoulder from clavicle to clavicle. A major advantage of this harness construction is that this feature provides compression forces over the shoulders and neck areas. The closure of the shoulder harnesses open and close on-demand and allows the medical staff to place the improved dressing on the body immediately after surgery while the male or female patient remains on the operating room table. The compression forces generated by such shoulder harness constructions help to prevent bleeding after surgery and provide greater support for the recovering patient generally.

8. Each embodiment of the present invention requires a front closure such that the improved dressing may be easily placed and positioned on the torso after the surgery; and yet allow repeated access and easy examination by the physician to the chest areas at or around the surgical incision site. Moreover, the front closure allows the patient to adjust the positioning of the improved dressing on his or her own body at will without requiring the assistance of a nurse or attendant.

9. The present invention also optionally provides an improved dressing with a loop or pocket of reinforced fabric disposed anywhere on the elastomeric material constituting the exterior fabric surface of the garment. This loop of reinforced fabric or pocket will support and hold the collection bulb frequently found in drainage assemblies and systems. As the drainage fluid collects and accumulates within the bulb, the increasing weight of the collection bulb is held and supported by the dressing material itself; and the collection bulb remains attached and secured by the dressing over the entirety of the time that the drain or drainage system is in place within the surgical incision site. As a consequence of this optional feature and construction, the inherent dangers of displacing or rupturing the drainage system is effectively eliminated.

A First Preferred Embodiment

It will be recognized and appreciated that the present invention is a garment which may be worn on the torso—that is, the trunk of the body without covering the head or extremities. The surface area of the body trunk or torso which is to be covered will vary with the dimensions and configuration of the improved dressing actually constructed. Thus, for descriptive and illustrative purposes, it is desirable to employ a specific surgical site as one particular example of how the present invention may be employed to advantage; and by providing an improved dressing of dimensions and configurations which satisfy the needs of this specific example, to demonstrate clearly and more easily the structural features and unusual capabilities provided by the present invention which exist generally in a variety of different use circumstances.

Accordingly, for descriptive and illustrative purposes alone, the detailed disclosure herein will limit itself primarily to a female patient which has undergone a mastectomy on her left breast. It will be clearly understood and recognized, however, that the discussion which focuses on a surgical incision site on the left female breast does not restrict or limit the uses or construction of the present invention to female patients or to this single application. To the contrary, the reader will recognize and be aware that any chest wall surgery as such for either a male or female patient is directly applicable and included by the detailed disclosure.

One preferred embodiment of the present invention is illustrated by FIGS. 1–5 respectively. FIG. 1 shows an embodiment of the improved dressing as a completely integral construction prior to being worn by the patient; and FIGS. 2–5 illustrate the manner and placement of the present invention on the torso of the female patient immediately after the left breast mastectomy has been completed and the incision covered with a gauze bandage.

FIG. 1 shows one preferred embodiment of the deformable, compression-generating dressing 10. By definition, a deformable construction and garments is one which will be altered temporarily in size, volume, and configuration when placed under the influence of compression forces or expansion forces; and will revert and return substantially to its original size, shape, state and status when the compression or expansion forces are subsequently removed or released. A wide range and choice of synthetic elastomeric materials may be used as the deformable fabric of the improved dressing 10. These include polyurethane base elastomers (such as SPANDEX, LYCRA; and VYRENE); polyester based elastomers (such as ESTANE); olefin based elastomers (such as NASTIN); and vinyl polymer based elastomers. All of these synthetic elastomeric materials are conventionally known and appear in a large variety of different chemical formulations and fabrications. All of these conventionally known materials are deemed to be within the scope of the present invention. Similarly, the fabric of the improved dressing comprising the present invention may provide a blending of elastomeric materials with other fabrics and fibers. These blending materials may include natural and synthetic fibers and textiles such as cotton, linen, flax, ramie, rayon, and high bulk acrylics. It is most desirable that the fibers and materials employed, blended or unblended, provide a soft and smooth fabric and textile which is biocompatible and non-irritating against the skin of the torso. Similarly, the degree of elasticity and the consequent compression forces generated will each vary substantially with the choice of elastomeric materials chosen and the elastic properties of the fabric actually employed for the manufacture of the garment itself.

As seen in FIG. 1, the drainage accommodating, compression generating dressing 10 comprises an integral one-piece torso compression bandage 12, first and second shoulder bands 30, on-demand closure means 40, and a deformable cutout zone 50. Each of these will be described in detail.

The torso compression bandage 12 is to be worn by a patient after surgery to cover and compress at least one surgical incision site in the torso and is formed at least in part of deformable elastomeric material for the generation of compression forces at the surgical incision site and the surrounding torso areas. The torso compression bandage 12 itself is comprised of an elongated back compression panel 14; first and second compression side sections 16a and 16b; and discrete first and second breast and chest compression overlay portions 18a and 18b. The elongated back compression panel 14 is of fixed dimensions and configurations sufficient to cover and compress at least part of the wearer's back. Thus, the length and width of the back compression panel 14 bear direct relation to the girth of the torso such that the patient is not uncomfortably restricted as a result of wearing the improved dressing.

The first and second compression side sections 16a and 16b respectively are each adjacently joined and integrated with the back compression panel 14. These first and second compression side sections 16a and 16b are also of fixed dimensions and configuration sufficient to cover and compress at least part of the sides of the wearer's torso. Accordingly, the dimensions of the side sections 16a and 16b should take notice and regard of the patient's body dimensions for maximum comfort and fit. The discrete first and second breast and chest compression overlay portions 18a and 18b are each separately attached and integrated with one of the compression side sections 16a or 16b respectively. Moreover, when the first and second breast and chest compression overlay portions 18a and 18b are physically joined together by the closure 40, the overlay portions 18a and 18b provide a joined overlay of fixed dimensions and configuration which is sufficient to cover and compress the breasts and at least part of the chest area of the wearer's torso.

The first and second shoulder bands 30a and 30b comprise a plurality of flexible members 32a, 34a, 32b, and 34b respectively. As shown in FIG. 1, the flexible members 32a and 34a constitute first shoulder band 30a; similarly, flexible members 32b and 34b constitute second shoulder band 30b. Attached to the ends of flexible members 32a and 32b are loops 36a and 36b respectively through which the members 34a and 34b will pass individually and then become adherent to itself via VELCRO brand of hook and pile loop fasteners 38. In this manner, the member 34a will pass through loop 36a attached to member 32a and adhere to itself to form the shoulder band 30a. Similarly, member 34b will pass through loop 36b of member 32b and adhere to itself to form the second shoulder band 30b.

In this first preferred embodiment, it will be noted and understood that while the torso compression bandage 12 and its integrated component parts (including the back compression panel 14, first and second compression side sections 16a and 16b, as well as first and second breast and chest compression overlay portions 18a and 18b respectively) are each formed of deformable elastomeric materials at least in part, the first and second shoulder bands 30a and 30b typically are not formed of elastomeric matter. Thus, in this embodiment, the shoulder bands do not generate any compression force of consequence or value; and these shoulder bands serve merely as an over-the-shoulder anchorage when the improved dressing 10 is placed on the torso of the female patient. It will be appreciated also that any other conventionally known manner of joining the flexible members 32a and 34a to form a first shoulder band as well as the joining of flexible members 34b and 32b to form a second shoulder band may be substituted for the loops 36 and the VELCRO brand of hook and pile loop fasteners 38. All such conventional means for linking and unlinking the flexible members to form individual shoulder bands is deemed to be conventionally known and therefore is encompassed within the scope of the present invention.

The closure means 40 shown of FIG. 1 comprise Velcro fasteners and provide a single front closure for the garment. VELCRO brand of hook and pile loop fasteners 40a and 40b comprise alternative and opposite parts of a single fastener which will bind together when placed in physical contact or proximity in the conventionally known manner. This VELCRO brand hook and pile loop type of fastener is most preferred as a front closure for the improved dressing because it is the easiest and most comfortable form of fasteners and closure, requiring little or no effort by the patient, and yet providing a strong and secure physical linkage on-demand. In the alternative, any of the other conventionally known kinds of fasteners including hook and eye, snaps, buttons and button holes, spindles and eyelets, and the like may be employed if desired or required under specific circumstances. In each instance, however, it is required that the closure means employed be able to attach and detach the first and second breast and chest overlay portions 18a and 18b together at will or on-demand-to form a joined overlay of fixed dimensions and configuration which is adequate and sufficient to cover and compress the breasts and at least part of the chest area of the torso.

Another requisite structural feature and component part of the present invention is the presence of at least one deformable cutout zone within the elastomeric material of the torso compression bandage. As illustrated by FIG. 1, a cutout zone 50 is shown which comprises three individual and different component parts: an expandable and contractible aperture 52, at least one elastic and compression generating marginal edging 54 and on-demand juncture means 56. The aperture 52, being a hole or opening in the elastic fabric of the torso compression bandage 12 is expandable and contractible; and the perimeter and size of the aperture will vary with the nature and degree of expansion or contraction. When the improved dressing 10 of FIG. 1 is manufactured and ready for use, the configuration and volume of the aperture is that present in the original construction and unaltered state. However, when the improved dressing is positioned on the torso and worn by the patient, the aperture will expand and subsequently become forcefully contracted in the manner described hereinafter. Thus, in both the expanded and contracted states, the aperture provides passage for at least one surgical drain extending from the surgical incision site through the torso compression bandage 12 to the external ambient environment.

Delineating and defining the configuration, perimeter, and size of the aperture 52 in the unworn garment state, in the expanded state, and in the contracted state, is at least one elastic and compression generating marginal edging 54. This marginal edging 54 typically is a reinforcement of the elastic material constituting the torso compression bandage 12 and provides compression forces along at least one part of the perimeter of the aperture 52 in both the expanded and contracted states.

Lastly, on-demand juncture means 56 are disposed upon the torso compression bandage 12 adjacent to the marginal edging 54; and provide for on-demand joining of a part of the marginal edging 54 to the fabric of the torso compression bandage 12 such that the aperture 52 becomes contracted and an additional compression force is generated along the joined part of the marginal edging. Although a number of different structures and styles of on-demand juncture means are conventionally known and available for use in the present invention, a preferred format is the use of VELCRO brand hook and pile loop fasteners 58a and 58b. Fastener portion 58a is mounted directly onto the elastic fabric forming the torso compression bandage 12 and is positioned adjacent to one segment 56a of the marginal edging. Similarly, the other fastener part 58b of the VELCRO brand hook and pile loop fastener 58 is mounted on the elastic fabric of the torso compression bandage 12 adjacent to another segment 54b of the marginal edging and is a loose strap which can be joined at will to its opposite fastener part 58a.

Figure 2:
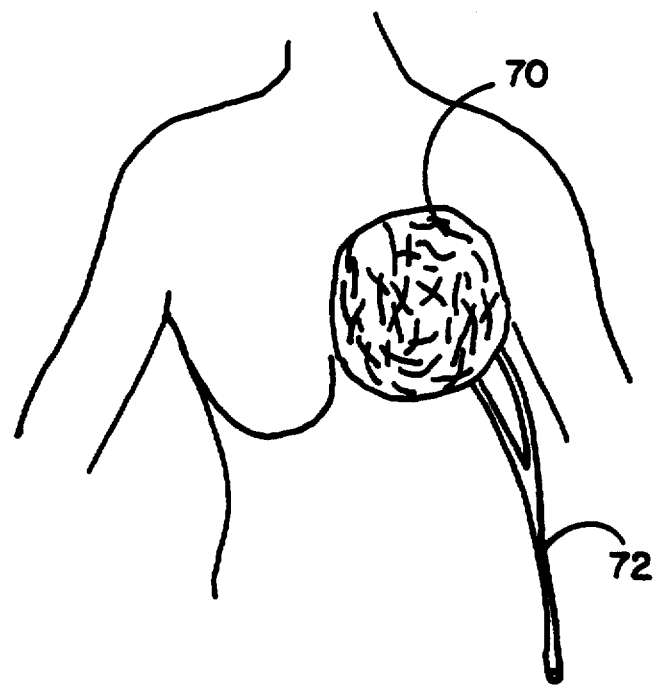
FIG. 2 is a front perspective view of a woman with gauze on her chest after chest wall surgery, a mastectomy on the left breast.

The unique structural features, capabilities and advantages of the dressing 10 are demonstrated by FIGS. 2-5 respectively which illustrate the placement and matter of wearing by the female patient. FIG. 2 illustrates the female patient immediately after the surgical procedure (the left breast mastectomy) has been completed, and shows a gauze bandage 70 covering the breast of the patient and a Y-shaped surgical drain assembly 72 extending from the surgical incision site in the left breast through the gauze 70.

Figure 3:
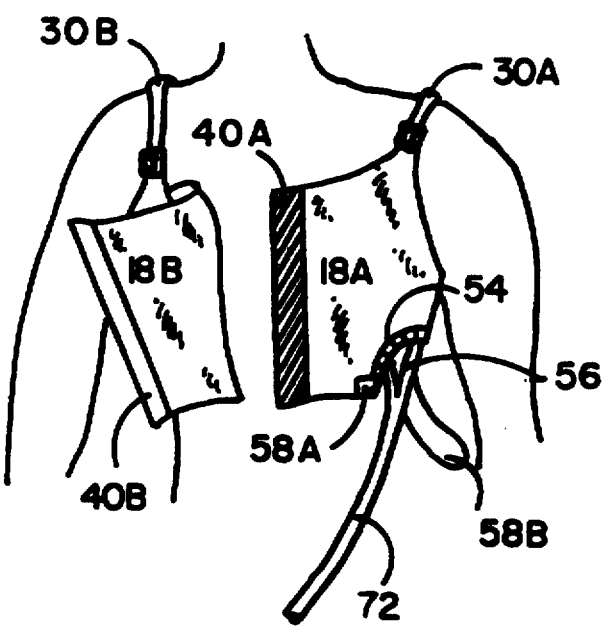
FIG. 3 is a front perspective view of the first preferred embodiment of FIG. 1 hanging loosely on the woman's torso in an open condition.

As illustrated by FIG. 3, the improved dressing 10 of FIG. 1 is placed on the torso of the patient and is being positioned properly for the benefit of the patient. FIG. 3 shows the improved dressing 10 hanging loosely from the shoulders of the female patient via the first and second shoulder bands 30a and 30b. The cutout zone 50 appears in position within the fabric constituting side section 16a and breast and chest overlay portion 18a. Thus, even though the improved dressing 10 has not yet been fastened on the torso and remains hanging loosely from the shoulders, surgical drain 72 is easily placed to lie within aperture 52 of the cutout zone 50. Equally important, no compression force whatsoever has been generated by the improved dressing 10 and there is no dislocation or disruption of the fluid flow within the drain 72.

Figure 4:
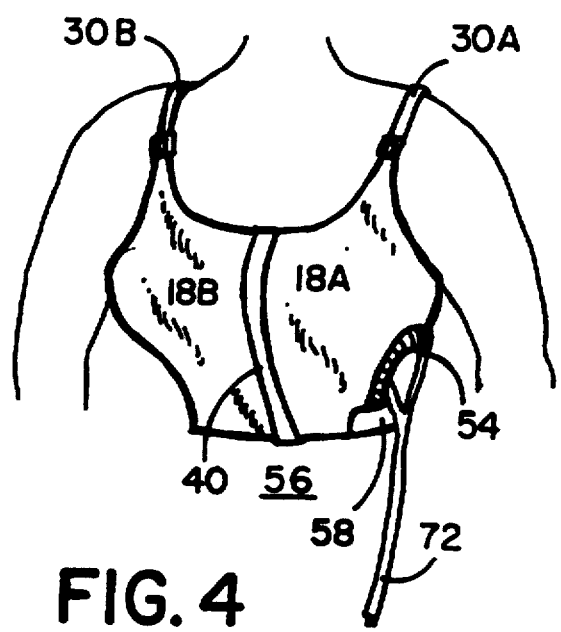
FIG. 4 is a front perspective view of the first preferred embodiment of FIG. 1 in a closed condition on the woman's torso.

FIG. 4 illustrates the manner of wearing and using the improved dressing 10 after the first and second breast and chest overlay portions 18a and 18b have been joined together using the closure means 40. Compression forces are generated around the entirety of the torso compression bandage 12 when the breast and chest overlay portions are joined. However, the surgical drain 72 passing through aperture 52 of the cutout zone 50 remains unhindered and unconstricted as it exits into the ambient environment. In order to generate additional compression force completely around the exiting drain 72, fastener part 58b has been pulled across the aperture 52 and joined to its opposite fastener 58a as a complete juncture. It will be recognized and appreciated, therefore, that the aperture 52 initially expanded when the improved dressing was fastened together via closure means 40; and then became forcefully contracted when fastener portion 58b was pulled to the left and joined to fastener portion 58a forming a completely joined and self-attaching fastening.

Figure 5:
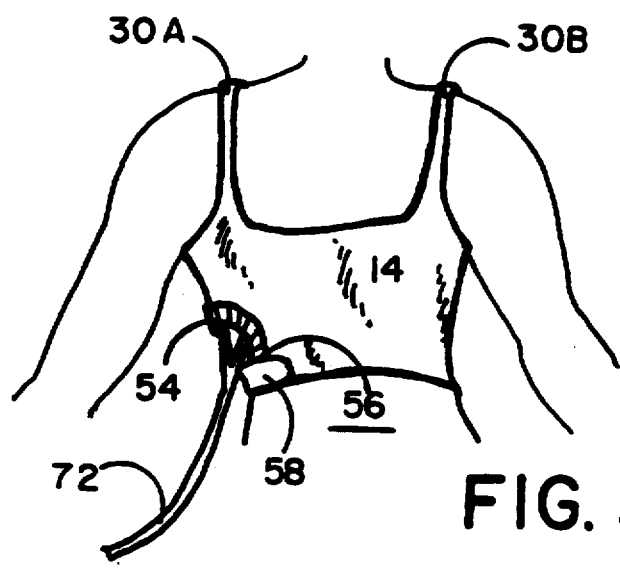
FIG. 5 is a rear perspective view of the first preferred embodiment of FIG. 4.

This last point is well illustrated by FIG. 5 in conjunction with FIG. 4 and provides the rear and front views of the improved dressing when properly worn and positioned. The fastener part 58b extends over the bottom of the aperture 52 and across the marginal edging 54 to link and be bound to its opposite fastener part 58a. Also, when the fasteners are joined to one another, marginal edging segment 54b is physically moved closer to marginal edging segment 54a—with the consequence that the aperture 52 is forced into a contracted state and there is an additional compression force generated along the axis of juncture created by the joining of the fasteners 58a and 58b respectively.

A more detailed illustration of the expansion and contraction feature of the aperture 52 and the marginal edging 54 comprising the cutout zone 50 is shown by FIG. 6. The expanded state for the aperture 52 (and the marginal edging 54) is illustrated by FIG. 6A which is in an expanded condition with respect to the aperture and marginal edging as it appears within FIG. 1 for the unworn garment. Clearly, once the garment 10 is properly positioned on the torso and the closure means 40 employed, the aperture 52 expands in size and configuration in the manner and degree illustrated by FIG. 6A. Subsequently, when the fastener 58 is employed and fastener part 58a joined to fastener 58b, the physical act of joining these fastener pads together forces the aperture 52 to diminish in size from its expanded condition into a contracted state; and concomitantly forces the marginal edging segments 54a and 54b closer together.

This forcible contraction of the aperture 52 and the marginal edging 54 causes an additional compression force to be generated and applied along the axis A—A' as seen in FIG. 6B. In this manner, the surgical drain 72 passing and exiting through aperture 52 in both the expanded and contracted states, becomes surrounded and completely encompassed by compression forces along the entirety of the perimeter of aperture 52. Moreover, the initial absence of compression force along the axis A—A' when the aperture 52 is in the expanded state illustrated by FIG. 6A—which exists because of the hole in the edge of the torso compression bandage 12 created by the existence of the cutout zone 50—is removed and compensated for by the physical action of the joining the fasteners 58a and 58b to each other. In this manner, the creation and generation of additional compression forces along the axis A—A' provides compression force completely around the exit for the surgical drain 72 and provides for the overall improvement and recovery of the patient.

This feature and capability of expanding and contracting the aperture and marginal edging can be achieved using a variety of different structural formats other than VELCRO brand hook and pile loop fasteners. Alternative embodiments are shown by FIGS. 7 and 8 respectively. Thus, FIG. 7 shows on-demand juncture means disposed upon the torso compression bandage 12 adjacent to the marginal edging 54 for on-demand joining. The specific juncture means shown comprises a hook 80 and eyelet support 82. The hook 80 has a curved portion 84 and is joined directly to the elastic fabric of the dressing via swivel 86. The eyelet 82 is a conventionally grooved shaft shaped in size and dimensions to accommodate the curved portion 84 of the hook 80. As shown by FIG. 7A, when the improved dressing is properly positioned and closed on the torso, the aperture 52 and marginal edging 54 are forced into an expanded state in comparison to the perimeter and size of the aperture in the unworn garment. Subsequently, when the wearer pulls the hook 80 across and joins it to the eyelet 82 as shown by FIG. 7B, the act of joining the hook to the eyelet forces the aperture 52 and the marginal edging 54 from an expanded condition into a contracted state. Both the perimeter and size of the aperture become reduced markedly; and the marginal edging segments 54a and 54b are brought into close proximity to each other.

Another alternative embodiment and manner of on-demand juncture means is shown by FIG. 8 which utilize a strap 90 and buckle 92 in combination for closure. As shown by FIG. 8A, the strap 90 is mounted directly on the fabric of the improved garment adjacent to marginal edging segment 54b while the buckle 92 is mounted directly on the elastomeric fabric adjacent marginal edging segment 54a. When the improved dressing is positioned and closed on the torso, the aperture 52 and the marginal edging 54 appear in the expanded condition illustrated by FIG. 8A. Subsequently, when strap 90 is threaded through buckle 92 and pulled through to achieve closure, the result is illustrated by FIG. 8B which shows the act of closure forcing the aperture 52 and the marginal edging into a contracted state. Similarly, as shown collectively by all embodiments of FIGS. 6, 7, and 8 respectively, the act of closure creates an additional compression force along the axis A—A'. In this manner, the perimeter of the aperture becomes encompassed and surrounded by compression forces along the entirety of its perimeter.

It will be recognized and appreciated also that any physical means or construction which constitutes and provides on-demand junctures means may be advantageously used with the present invention; and that the specific embodiments of FIGS. 6, 7 and 8 are mere representative and illustrative of the many conventionally known formats and structures available. Thus, other alternative on-demand juncture means for the cutout zone may include buttons and loops; eyelets and loops; buttons and button holes; open eyelets and interlacing strings; and overlapping snaps and straps. All of these conventionally known alternatives ere deemed to be within the scope of the present invention.

Figure 10:
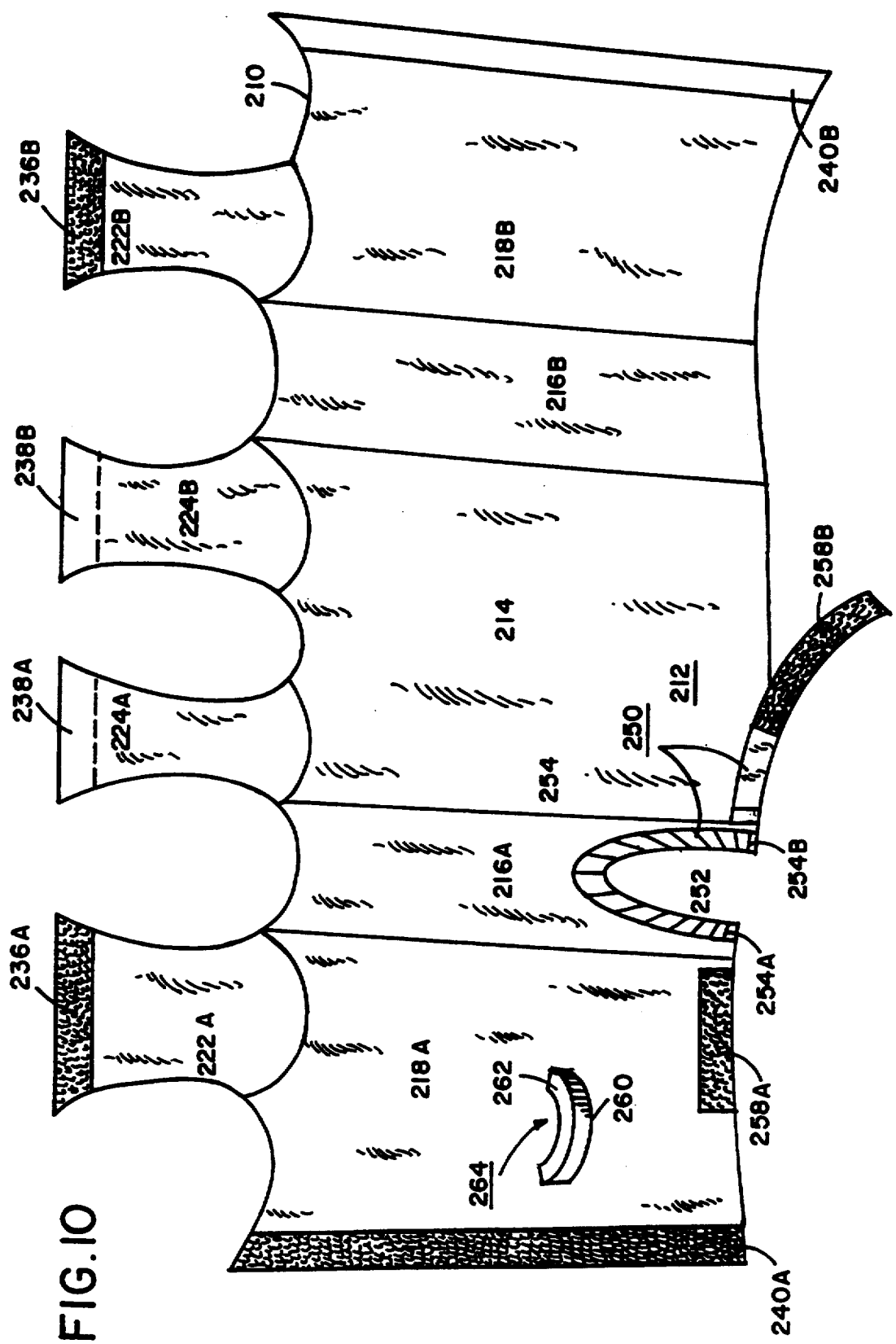
FIG. 10 is a front overhead view of a second preferred embodiment of the present invention.

In each and every embodiment of the present invention, a cutout zone comprising the minimal three component pads of an aperture, a marginal edging, and on-demand juncture means must be present. However, the physical appearance of the cutout zone, and its dimensions and its configuration may be varied radically from embodiment to embodiment. Moreover, the choice of where to place or position the cutout zone is a matter of discretion and choice dictated by the use circumstances of the surgery or the individual desires of the patient. It will be recognized, therefore, that the cutout zone may be positioned anywhere within the deformable elastic fabric constituting the improved garment itself. Thus, the cutout zone may be positioned within the back compression panel; or within the first and second compression side sections; or within the discrete first and second breast and chest compression overlay portions. The best and preferred positioning, However, for the cutout zone generally is at the edges of the elastic fabric forming the improved dressing as illustrated by FIGS. 1, 9, and 10 hereof. This edge or margin placement for the cutout zone is most desirable because of the considerable loss of compression force intrinsically created by the making of an exit Bole or opening along the outer seams of the improved dressing. This unique capability to exert an additional compression force is most beneficial along the outer edges and seams of the improved garment because there is no additional elastic material forming the garment to provide any force whatsoever when the aperture opening is at the outer edge extremities.

It will be recognized also, that there is no demand or requirement that merely a single cutout zone exist within the elastomeric material of the torso compression bandage. In many embodiments, two or more individual cutout zones will be present to accommodate more than one fluid drainage system: or to provide for fluid drainage assemblies on a left or right orientation basis-in the absence of knowing in advance where the surgery is to be performed for a specific patient. The presence of multiple cutout zones, However, does not cause any meaningful loss of compression force generation within the improved dressing as an integral garment. To the contrary, the existence of on-demand juncture means as a requisite part of each and every cutout zone ensures and provides for the generation of additional compression forces at each and every location where a cutout zone appears in the garment.

It is also desirable for the reader to recognize the range and variety of configurations, sizes, volumes, of cutout zones which are permissible and advantageous for use. These are represented and illustrated by FIG. 9 in which only the aperture 152 and marginal edging 154 are shown for purposes of clarity. Note that each of FIGS. 9A, 9B, 9C, 9D and 9E respectively illustrate and exemplify an aperture and marginal edging in alternative formats. FIGS. 9A-9E may be usefully compared with the aperture 52 and marginal edging 54 of FIG. 1 which constitute a preferred embodiment of the cutout zone. Accordingly, the preferred cutout zone of FIG. 1 provides a bullet shaped aperture approximately one inch high and about three-quarters of one inch wide-which is defined and delineated by a rim of reinforced elastic fabric. However, as illustrated by the embodiments of FIG. 9, the cutout zone may take any regular or irregular, symmetrical or asymmetrical, geometric or non-geometric, and coherent or non-coherent configuration, size, or dimensions.

A Second Preferred Embodiment of the Invention

An alternative construction for the drainage accommodating compression dressing comprising the present invention is illustrated by FIGS. 10-14 respectively. FIG. 10 shows an improved dressing 210 of fixed dimensions and configurations sufficient to cover almost the entire torso of the wearer after the garment has been properly positioned and closed on the body. The positioning of the dressing and the beneficial consequence of wearing it is illustrated by FIGS. 11-14.

The torso covering compression dressing shown by FIG. 10 is preferably manufactured from a single length of deformable elastomeric material using a dressmaker's template to yield the dimensions and overall configuration shown. Alternatively, multiple pieces of deformable elastomeric material may be sewn or otherwise bonded together to form an integral one-piece torso compression bandage 212 to be worn by a patient after chest wall surgery to cover and compress at least one surgical incision site in the torso.

The integral torso compression bandage 212 comprises an elongated back compression panel 214 of fixed dimensions and configuration sufficient to cover and compress most of the wearer's back. Adjacently joined to the back compression panel 214 are first and second compression side sections 216a and 216b. These first and second compression side sections 216a and 216b are of fixed dimensions and configuration adequate and sufficient to cover and compress almost all of the sides of the wearer's torso. Separately and individually attached to one of the compression side sections 216a and 216b are discrete first and second breast and chest compression overlay portions 218a and 218b. These first and second breast compression overlay portions 218a and 218b can at will be joined together to provide a joined overlay of fixed dimensions and configuration adequate and sufficient to cover and compress both the breasts and almost the entirety of the chest area of the torso. The major difference between the torso compression bandage 212 of FIG. 10 and the torso compression bandage 12 of FIG. 1 thus lies primarily in the greater dimensions and surface area of fabric provided by this second preferred embodiment which permits almost the entirety of the back, sides, breast and chest of the wearer's torso to be covered and compressed by the improved brassiere.

Disposed upon the first and second breast and chest compression overlay portions 218a and 218b of the torso compression bandage 212 are on-demand closure means 240 comprising VELCRO brand hook and pile loop fastener pads 240a and 240b respectively. These fastener parts 240a and 240b may be attached and detached repeatedly at will to close the torso compression bandage 212a and consequently will generate compression force over almost the entirety of the torso. In addition, a deformable cutout zone 250 exists within the elastomeric material of the torso compression bandage 212. The cutout zone 250 comprises an expandable and contractible aperture 252, the perimeter and size of which in both the expanded and contracted states provides passage for at least one surgical drain from within the surgical incision site through the torso compression bandage to the external ambient environment; comprises an elastic and compression generating marginal edging 254 delineating the perimeter and size of the aperture 252 in both the expanded and contracted states and providing compression forces along at least one part of the perimeter of the aperture in the expanded and contracted states; and comprises on demand juncture means 258 formed as a VELCRO brand hook and pile loop fastener using fastener pads 258a and 258b. The on-demand juncture means 258 are disposed on the fabric of the torso compression bandage 212 adjacent to the marginal edging 254 for at will joining of a part of the marginal edging to a portion of the torso compression bandage—whereby the aperture 252 becomes contracted and an additional compression force is generated along the joined part of the marginal edging. The cutout zone 250 of FIG. 10 thus is substantially similar in construction and in function to that appearing within FIGS. 1 and 6 respectively.

An additional unique feature of this preferred second embodiment of the present invention is the existence and use of first and second shoulder compression harnesses 220a and 220b—which are individually attached to the back compression panel 214 and which are individually joined to one of the breast and chest compression overlay portions 218. Each of the first and second shoulder compression harnesses 220a and 220b comprises a plurality of extendible flap members 222a, 224a, 222b, and 224b respectively. These flap members are formed at least in part of elastomeric material; and each has fixed dimensions and configuration adequate and sufficient to generate a compression force over at least a part of the shoulders and upper chest of the wearer's torso. Each shoulder compression harness 220a and 220b also comprises means for attaching and detaching a pair of flap members (222a with 224a as well as 222b with 224b) to each other on-demand. A preferred means for attachment and detachment on-demand are VELCRO brand hook and pile loop fasteners 236 and 238 comprising fastener portions 236a, 238a as a first pair and fastener portions 238b with 236b as a second pair. In this manner, each of the shoulder harnesses may be opened and closed repeatedly at will by the wearer whenever desired or required under the circumstances.

Another unique feature of this second preferred embodiment is the presence of a drain support 260 which retains and holds a collection bulb such as is typically present within a surgical drainage apparatus. The drain support 260 is formed as an elastic loop of reinforced fabric 262 which typically is attached directly to the torso compression bandage 212 for holding and securing a collection bulb. The support 260 may be a freely dangling loop attachable directly to the drainage collection bulb; or may exist as a joined patch of fabric attached to the fabric of the dressing in the form of a pocket. The loop 262 thus provides either a pocket or expansion linkage 264 which will expand and contract to conform with the overall dimensions of almost all collection bulbs conventionally employed in a drainage apparatus or assembly.

The value and purpose of the drain support 260 is to hold and secure the collection bulb as ever greater amounts of drainage fluid are collected after surgery in the recovery and convalescent time periods. By holding and securing the collection bulb in this manner, the weight and awkwardness of the drainage assembly is carefully controlled and reduced-adding to the security of the drainage system and greatly increasing the comfort and ease for the patient.

Figure 11:
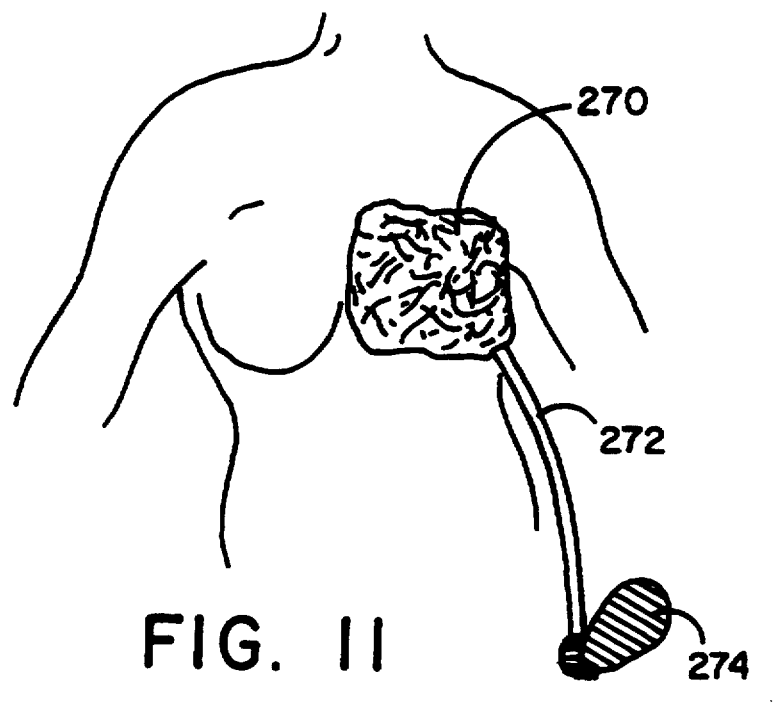
FIG. 11 is a front perspective view of a woman with gauze on her chest after undergoing a mastectomy on her left breast.
Figure 12:
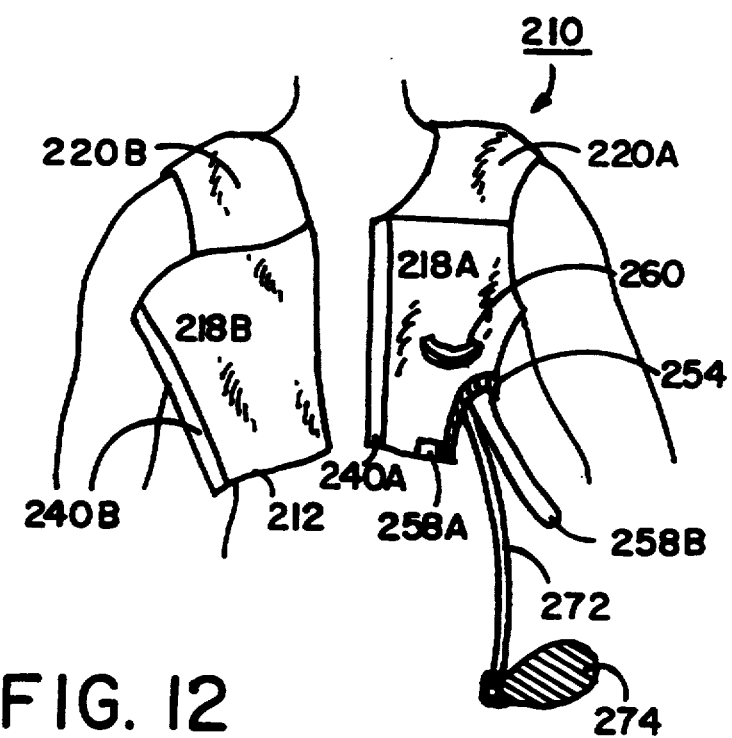
FIG. 12 is a front perspective view of the second preferred embodiment of FIG. 10 hanging loosely on the woman's torso in an open condition.

The intended manner of using and wearing this second preferred embodiment of the improved dressing is illustrated by FIGS. 11-14 respectively. FIG. 11 shows the illustrative example employed herein of a woman who has undergone a mastectomy on her left breast; and appears as a recovery patient wearing a gauze bandage 270 which covers her left breast. Extended from the surgical incision site in her left breast through the gauze 270 is a Y-shaped drain 272 which is in fluid flow communication with a collection bulb 274. FIG. 12 shows the second preferred embodiment of the present invention worn loosely on the shoulders by the female patient while the torso compression bandage remains open. At this moment therefore, there are no compression forces generated over the torso because the garment has not yet been properly positioned and closed on the body. Moreover, the Y-shaped drain 272 has been placed through the aperture 252 of the cutout zone 250 and hangs loosely of its own weight without restraint of any kind.

Figure 13:
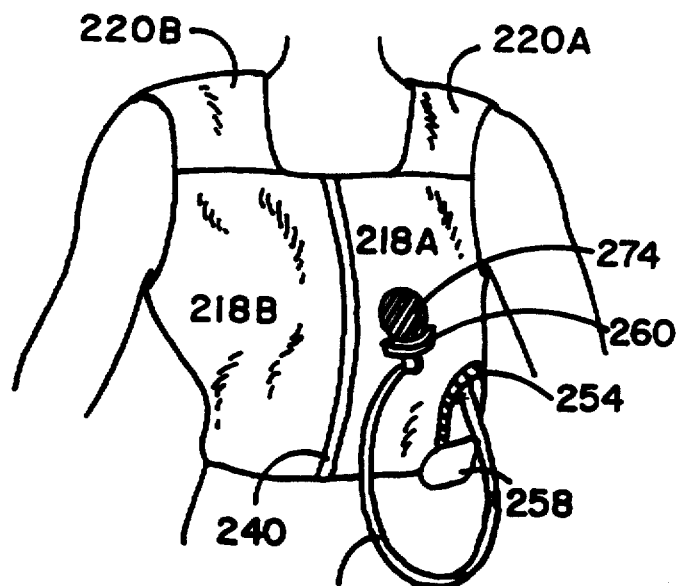
FIG. 13 is a front perspective view of the second preferred embodiment of FIG. 10 in a closed condition on the woman's torso.
Figure 14:
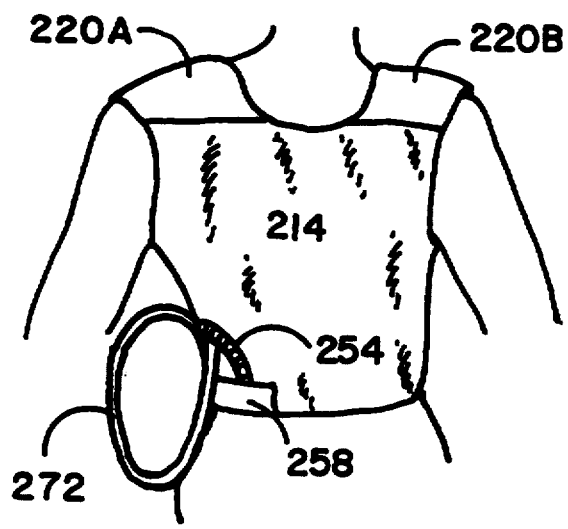
FIG. 14 is a rear perspective view of the second preferred embodiment of FIG. 13.

The improved dressing 210 in a fully closed format, properly positioned and worn by the female patient is illustrated by FIGS. 13 and 14 respectively. The front view provided by FIG. 13 shows that the breast and chest overlay portions have been joined to create a joined overlay; and consequently, compression force has been generated at the back, at the sides and over the breast and chest of the wearer by the garment. In addition, the shoulder compression harnesses 220a and 220b are in correct position with the flap members attached and closed to each other to provide a complete covering over the shoulders and upper chest. In this position the shoulder harnesses generate additional compression force over the entirety of each shoulder, and over the upper chest and upper back of the wearer.

In addition, the on-demand juncture means 258 of the cutout zone 250 has been properly positioned and closed around the exiting drainage assembly 272 such that the aperture 252 has become contracted and considerable addition compression force has been generated along the joined part of the marginal edging 254. The collection bulb 274 has also been purposefully placed within the drain support 260 and is held and secured in proper position by the expandable loop 262. Thus as the drainage fluid exists the surgical incision site, the drain support 260 will hold and secure the collection bulb 274 thereby reducing the weight and providing support for the existing drainage system as it extends into the ambient environment. FIG. 14 shows a rear view of the Y-shaped drain 272 as it passes through the aperture 252 of the cutout zone 250.

The present invention is not to be restricted in form nor limited in scope except by the claims appended hereto.

What I claim is:

1. A post-surgical, drainage accommodating, compression dressing defining:

an integral one-piece torso compression bandage to be worn by a patient after surgery to cover and compress at least one surgical site on the torso, and concurrently to accommodate the passage on-demand of at least one surgical drain extending from the surgical incision site through said torso compression bandage, and formed at least in part of deformable elastomeric material to generate compression forces at the surgical incision site and the surrounding torso areas, said torso compression bandage comprising:

(A) a compression panel including:
  (a) a back overlying compression area sufficient to cover and compress at least part of wearer's torso,
  (b) first and second side overlying compression area sufficient to cover and compress at least part of a respective side of the wearer's torso, and
  (c) first and second breast and chest overlying compression areas, each of which extends from a respective one of said side overlying compression areas and which when joined together provide a joined overlay area sufficient to cover and compress at least part of the breast and chest of the wearer's torso; and (B) at least on deformable cutout zone within a respective one of said side overlying compression areas of said torso compression bandage to accommodate the passage on-demand of a surgical drain extending from a surgical site through said torso compression bandage, said deformable cutout zone comprising:
  (1) an expandable and contractible deformable aperture in said torso compression bandage, the perimeter and size of said deformable aperture in both the expanded and contracted states accommodating on demand passage for at least one surgical drain from the surgical incision site on the torso through said torso compression bandage,
  (2) at least one elastic and compression generating marginal edging surrounding the perimeter and delineating the size of said deformable aperture in the expanded and contracted states, and
  (3) on demand compression generating juncture means disposed upon said torso compression bandage adjacent to said marginal edging and said deformable aperture for on-demand joining of a part of said marginal edging to said torso compression bandage, whereby said deformable aperture becomes contracted and additional compression force is generated on-demand along the joined part of said marginal edging.

2. The dressing of claim 1 additionally including:
first and second shoulder bands, each of which are individually joined to said back overlying compression areas, each of said first and second shoulder bands being extendible over a respective one shoulder of the wearer's torso.

3. The dressing of claim 1 additionally including:
on-demand closure means secured to said first and second breast and chest overlying compression areas for attaching and detaching said first and second breast and chest overlying compression areas to each other at will.

4. The dressing of claim 1 wherein each said cutout zone is positioned at the peripheral edge within a respective one of said side overlying compression areas.

5. A post-surgical, drainage accommodating, compression dressing defining:
an integral one-piece torso compression bandage to be worn by a patient after surgery to cover and compress at least one surgical incision site on the torso, and concurrently to accommodate the passage on-demand of at least one surgical drain extending from the surgical incision site through said torso compression bandage, and formed at least in part of deformable elastomeric material to generate compression forces at the surgical incision site and the surrounding torso areas, said torso compression bandage comprising:

(A) a compression panel including:
  (a) a back overlying compression area sufficient to cover and compress at least part of the wearer's torso,
  (b) first and second side overlying compression areas, each of which extends from a respective side of said back overlying compression area and is sufficient to cover and compress at least part of a respective side of the wearer's torso, and
  (c) first and second breast and chest overlying compression areas, each of which extends from a respective one of said side overlying compression areas and which when joined together provide a joined overlay area sufficient to cover and compress at least part of the breast and chest of the wearer's torso;

(B) first and second shoulder bands, each of which are individually joined to said back overlying compression area and are individually joined to a respective one of said first and second breast and chest overlying compression areas, each of said first and second shoulder bands being extendible over a respective one shoulder of the wearer's torso;

(C) on-demand closure means secured to said first and second breast and chest overlying compression areas for attaching and detaching said first and second breast and chest compression areas to each other at will; and (D) at least one deformable cutout zone within a respective one of said side overlying compression areas of said torso compression bandage to accommodate the passage on-demand of a surgical drain extending from a surgical incision site through said torso compression bandage, said deformable cutout zone comprising:
  (1) an expandable and contractible deformable aperture in said torso compression bandage, the perimeter and size of said deformable aperture in both the expanded and contracted states accommodatinq on-demand passage for at least one surgical drain from the surgical incision site on the torso through said torso compression bandage,
  (2) at least one elastic and compression generating marginal edging surrounding the perimeter and delineating the size of said deformable aperture in the expanded and contracted, states, and
  (3) on-demand compression generating juncture means disposed upon said torso compression bandage adjacent to said marginal edging and said deformable aperture for on-demand .joining of a part of said marginal edging to said torso compression bandage, whereby said deformable aperture becomes contracted and additional compression force is generated on-demand along the joined part of said marginal edging.

6. The dressing of claim 5 wherein each said cutout zone is positioned at the peripheral edge within a respective one of said side overlying compression areas.

7. A post-surgical, drainage accommodating, compression brassier comprising:

an integral one-piece torso compression bandage to be worn by a woman after surgery to cover and compress at least one surgical incision site on the torso, and concurrently to accommodate the passage on-demand of at least one surgical drain extending from within the surgical incision site to the ambient environment, and formed at least in part of deformable elastomeric material to generate compression forces at the surgical incision site and the surrounding torso areas while accommodating a surgical drain, said torso compression bandage being comprised of (A) at least a first compression panel comprising
  (i) a back overlaying compression area sufficient to cover and compress at least part of the wearer's back,
  (ii) side overlaying compression areas sufficient to cover and compress at least part of the wearer's sides, and
(B) at least a second compression panel joined to said first compression panel, said second compression panel comprising
  (i) discrete first and second breast and chest compression overlay portions each of which is separately attached to said first compression panel and which when joined together provide a joined overlay sufficient to cover and compress at least part of the breasts and the chest area of the wearer's torso,
  (ii) on-demand closure means disposed upon said first and second breast and chest compression overlay portions for attaching and detaching said first and second breast and chest compression overlay portions to each other at will;
first and second shoulder bands which are individually joined to said first and second compression panels of said torso compression bandage, each of said first and second shoulder bands being extendible over one shoulder of the wearer's torso; and
at least one deformable cutout zone positioned at the peripheral edge within one of said side overlaying compression areas of said torso compression bandage to accommodate the passage on-demand of a surgical drain extending from within a surgical incision site to the ambient environment, said deformable cutout zone comprising
  (A) an expandable and contractible deformable aperture in the material of said torso compression bandage, the perimeter and size of said deformable aperture in both the expanded and contracted states accommodating on-demand passage for at least one surgical drain from within the surgical incision site on the torso through one of said compression panels of said torso compression bandage to the ambient environment,
  (B) at least one elastic and compression generating marginal edging surrounding the perimeter and delineating the size of said deformable aperture in the expanded and contracted states before and after the accommodation of a surgical drain through said deformable aperture, and
  (C) on-demand compression generating juncture means disposed upon one of said compression panels of said torso compression bandage adjacent to said marginal edging and said deformable aperture for on-demand joining of a part of said marginal edging to said torso compression bandage whereby said deformable aperture becomes contracted and additional compression force is generated on-demand along the joined part of said marginal edging before and after the accommodation of a surgical drain through said deformable aperture.

8. A post-surgical, drainage accommodating, compression brassiere comprising:

an integral one-piece torso compression bandage to be worn by a woman after surgery to cover and compress at least one surgical incision site on the torso, and concurrently to accommodate the passage on-demand of at least one surgical drain extending from within the surgical incision site to the ambient environment, and formed at least in part of deformable elastomeric material to generate compression forces at the surgical incision site and the surrounding torso areas while accommodating a surgical drain, said torso compression bandage being comprised of (A) at least a first compression panel comprising
  (i) a back overlaying compression area sufficient to cover and compress at least part of the wearer's back,
  (ii) side overlaying compression areas sufficient to cover and compress at least part of the wearer's-sides, and
(B) at least a second compression panel joined to said first compression panel, said second compression panel comprising
  (i) discrete first and second breast and chest compression overlay portions each of which is separately attached to said first compression panel and which when joined together provide a joined overlay sufficient to cover and compress the breasts and at least part of the breasts and the chest area of the wearer's torso, and
  (ii) on-demand closure means disposed upon said first and second breast and chest compression overlay portions for attaching and detaching said first and second breast and chest compression overlay portions to each other at will;
first and second shoulder compression harnesses which are individually attached to said first and second compression panels of said torso compression bandage, each of said first and second shoulder compression harnesses comprising
  (A) a plurality of extendible flap members formed of elastomeric material sufficient to generate a compression force over at least a part of the shoulders and upper chest of the wearer's torso, and
  (B) means for attaching and detaching said flap members to one another on-demand; and
at least one deformable cutout zone positioned at the peripheral edge within one of said overlaying compression areas of said torso compression bandage to accommodate the passage on-demand of a surgical drain extending from within a surgical incision site to the ambient environment, said deformable cutout zone comprising (A) an expandable and contractible deformable aperture in the material of said torso compression bandage, the perimeter and size of said deformable aperture in both the expanded and contracted states accommodating on-demand passage for at least one surgical drain from within the surgical incision site on the torso through one of said compression panels of said torso compression bandage to the ambient environment, (B) at least one elastic and compression generating marginal edging surrounding the perimeter and delineating the size of said deformable aperture in the expanded and contracted states, said marginal edging providing compression forces along at least a part of the perimeter of said deformable aperture in the expanded and contracted states before and after the accommodation of a surgical drain through said deformable aperture, and (C) on-demand compression generating juncture means disposed upon one of said compression panels of said torso compression bandage adjacent to said marginal edging and said deformable aperture for on-demand joining of a part of said marginal edging to said torso compression bandage whereby said deformable aperture becomes contracted and additional compression force is generated on-demand along the joined part of said marginal edging before and after the accommodation of a surgical drain through said deformable aperture.

9. The compression dressing as recited in claim 7 or 8 wherein said on-demand closure means disposed upon said first and second breast and chest compression overlay portions comprises hook and pile loop fasteners.

10. The compression dressing as recited in claim 7 or 8 wherein said on-demand juncture means of said cutout zone comprises hook and pile loop fasteners.

11. The compression dressing as recited in claim 7 or 8 further comprising a drain support disposed on the fabric of said torso compression bandage.

* * * * *